United States Patent [19]

Fujieda

[11] Patent Number: 5,684,562
[45] Date of Patent: Nov. 4, 1997

[54] OPHTHALMIC APPARATUS

[75] Inventor: Masanao Fujieda, Toyohashi, Japan

[73] Assignee: Nidek Company, Ltd., Japan

[21] Appl. No.: 570,938

[22] Filed: Dec. 12, 1995

[30] Foreign Application Priority Data

Dec. 12, 1994 [JP] Japan .................. 6-332637

[51] Int. Cl.$^6$ .................................................. A61B 3/10
[52] U.S. Cl. ........................ 351/212; 351/247; 351/211
[58] Field of Search ............................. 351/205, 211, 351/212, 221, 247

[56] References Cited

U.S. PATENT DOCUMENTS

| | | | |
|---|---|---|---|
| 3,589,107 | 6/1971 | Ishikawa | 128/2 |
| 4,993,826 | 2/1991 | Yoder, Jr. | 351/212 |
| 5,214,456 | 5/1993 | Gersten | 351/212 |
| 5,357,294 | 10/1994 | Shimizu et al. | 351/212 |
| 5,469,234 | 11/1995 | Konishi | 351/212 |
| 5,500,697 | 3/1996 | Fujieda | 351/212 |

Primary Examiner—Huy Mai
Attorney, Agent, or Firm—Rossi & Associates

[57] ABSTRACT

An ophthalmic apparatus for measuring the shape of the cornea of the eye, capable of measuring the pupil in a natural state of vision is provided. An illuminating light source illuminates a cornea shape measuring pattern with red or infrared light to project an image of the cornea shape measuring pattern on the cornea of the eye, and a CCD camera picks up the image of the cornea shape measuring pattern formed on the cornea. A computer analyzes the image of the cornea shape measuring pattern to obtain data of the shape of the cornea and processes the data to calculate the regional curvatures of regions of the cornea. An intraocular illuminating light source illuminates the interior of the eye with red or infrared light, and the CCD camera picks up an image of a pupillary region illuminated by the light emitted by the intraocular illuminating light source and reflected by the interior of the eye. The computer analyzes the image of the pupillary region to obtain the data of the pupillary region and processes the data to determine the shape or the size of the pupil in a natural state of vision.

15 Claims, 9 Drawing Sheets

| | |
|---|---|
| S1 | ALIGN THE OPHTHALMIC APPARATUS WITH THE EYE |
| S2 | HAS THE IMAGE STORAGE SWITCH BEEN OPERATED ? |
| S3 | TURN ON THE INTRAOCULAR ILLUMINATING LIGHT SOURCE |
| S4 | STORE AN IMAGE OF THE PUPIL IN THE MEMORY |
| S5 | TURN OFF THE INTRAOCULAR ILLUMINATING LIGHT SOURCE |
| S6 | TRANSFER THE DATA OF THE IMAGE OF THE PUPIL TO THE FRAME MEMORY |
| S7 | TURN ON THE PLACIDO'S DISK ILLUMINATING LIGHT SOURCE |
| S8 | PICKUP IMAGES OF THE PLACIDO'S RINGS FORMED ON THE CORNEA AND STORE THE DATA OF THE IMAGE IN THE MEMORY |
| S9 | TURN OFF THE PLACIDO'S DISK ILLUMINATING LIGHT SOURCE |
| S10 | TRANSFER THE DATA FROM THE MEMORY TO THE FRAME MEMORY |
| S11 | DISPLAY THE IMAGES OF THE PLACIDO'S RINGS ON THE DISPLAY |
| S12 | IS THE PICTURE SATISFACTORY ? |
| S13 | DETECT AND STORE AN IMAGE OF THE OUTLINE OF THE PUPIL AND THE EDGE OF THE PUPIL |

FIG. 3(b)

| | |
|---|---|
| S14 | CALCULATE THE MEAN DIAMETER OF THE PUPIL AND THE POSITION OF THE CENTER OF THE PUPIL AND STORE THE CALCULATED DATA |
| S15 | DETECT THE EDGES OF THE IMAGES OF THE PLACIDO'S RINGS |
| S16 | CALCULATE THE CENTER OF THE CORNEA ON THE BASIS OF THE DATA OF THE IMAGES OF THE PLACIDO'S RINGS, AND CALCULATES THE DISTANCES BETWEEN THE CENTER AND EACH OF THE IMAGES OF THE PLACIDO'S RINGS FOR DIRECTIONS AT ANGLES OF 0° TO 359° TO THE REFERENCE LINE |
| S17 | CALCULATE THE REGIONAL CURVATURES OF REGIONS OF OF THE CORNEA ON THE BASIS OF THE DATA OF A SPHERE HAVING A KNOWN CURVATURE AND THE DATA OF THE DISTANCES BETWEEN THE CENTER AND EACH OF THE IMAGES OF THE PLACIDO'S RINGS FOR DIRECTIONS AT ANGLES OF 0° TO 359° |
| S18 | DISPLAY A COLOR PICTURE OF A CORNEAL CURVATURE DISTRIBUTION DETERMINED ON THE BASIS OF THE REGIONAL CURVATURES OF REGIONS OF THE CORNEA AND THE OUTLINE OF THE PUPIL IN A SUPERPOSED PICTURE AND NUMERICAL DATA |
| S19 | IS DATA TRANSMISSION NECESSARY ? |
| S20 | TRANSFER THE IMAGE OF THE PUPIL, THE DATA OF THE OUTLINE OF THE PUPIL, THE DIAMETER OF THE PUPIL, THE DATA OF THE REGIONAL CURVATURES OF THE CORNEA TO AN EXTERNAL APPARATUS |

FIG. 3(c)

FIG. 4(a)
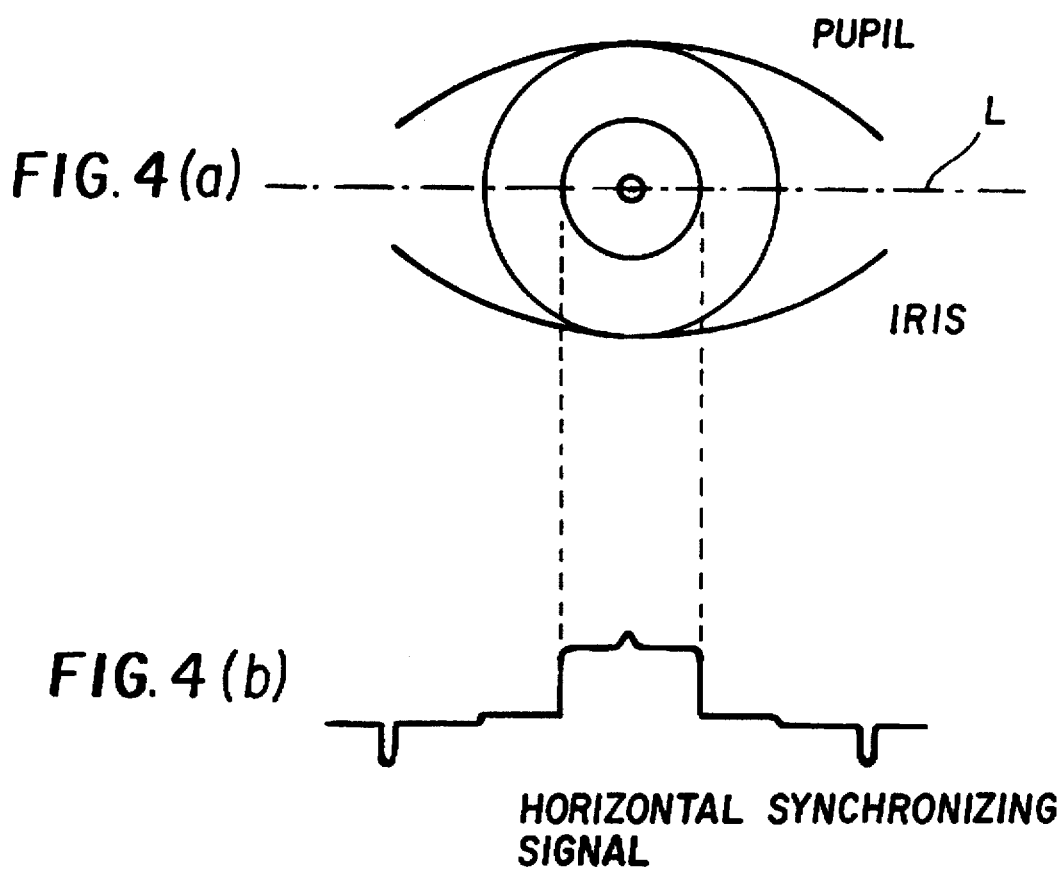
PUPIL
L
IRIS
FIG. 4(b)
HORIZONTAL SYNCHRONIZING SIGNAL
FIG. 4(c)
FIG. 4(d)
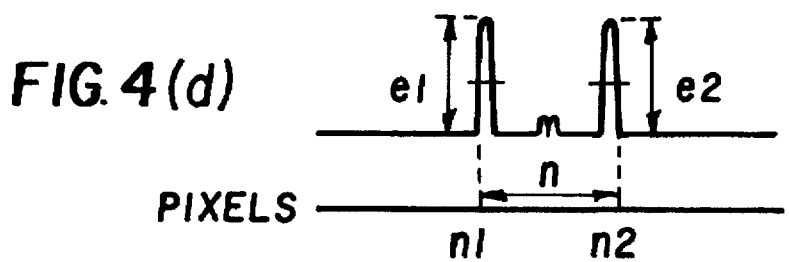
PIXELS

OPHTHALMIC APPARATUS

BACKGROUND OF THE INVENTION

1. Field of the Invention

The present invention relates to an ophthalmic apparatus for measuring the shape of the cornea of the eye.

2. Description of the Related Art

A known ophthalmic apparatus for measuring the shape of the cornea, i.e., a corneal topography system, measures the regional curvatures of a plurality of regions of the cornea and forms a corneal topographic map showing the distribution of the regional curvatures. This known ophthalmic apparatus projects a predetermined pattern formed on a Placido's disk or the like on the cornea, receives light reflected by the cornea by a CCD camera or the like to form an image of the cornea, analyzes the image of the cornea to determine a curvature distribution on the substantially entire cornea and displays the curvature distribution graphically on a monitor.

An ophthalmic apparatus of this type is used for obtaining information about the shape of the cornea before and after refractive surgery for correcting abnormal refraction, such as myopia hypermetropia or astigmatism. A refractive surgery changes the curvature of the cornea artificially by radially incising the surface of the cornea or partly ablating the surface of the cornea by using Excimer Laser(PRK). Information necessary for determining which region of the cornea must be incised or ablated is important as well as data representing the total refractive power of the eye and the curvature of the cornea. If the diameter of a portion of the cornea ablated by keratectomy is small as compared with the natural diameter of the pupil, i.e., the diameter of the pupil in a natural state of vision, an image formed on the retina causes diplopia or glare and cause visual difficulty. Therefore, a portion of a diameter greater than the natural diameter of the pupil must be incised or ablated by a refractive surgery. If an image of the pupil can be formed during the formation of a cornea-reflected image of the pattern of a Placido's disk, the positional relation between the cornea-reflected image and the pupil can be known. However, since the Placido's disk is illuminated with a fluorescent lamp and the pupil of the eye is in a miotic state, sufficiently effective information necessary for refractive surgery is not available.

SUMMARY OF THE INVENTION

Accordingly, it is an object of the present invention to provide an ophthalmic apparatus for measuring the shape of the cornea of the eye, capable of measuring the pupil without causing the contraction of the pupil.

In accordance with a first aspect of the present invention, an ophthalmic apparatus comprises: an index pattern projecting means for projecting the pattern of an index for measuring the shape of the cornea on the cornea; a first image pickup means for forming an image of the index; a cornea shape calculating means for calculating the respective shapes of regions of the cornea on the basis of the position of the image of the index determined by processing the image formed by the first image pickup means; a pupil illuminating means for illuminating the pupil of the eye with red light or infrared light; a second image pickup means for forming an image of the pupil illuminated by the pupil illuminating means; and a pupil measuring means for measuring the shape or the size of the pupil on the basis of the position of the edge of the pupil determined by processing the image formed by the second image pickup means.

The first image pickup means may be used also as the second image pickup means.

In accordance With a second aspect of the present invention, an ophthalmic apparatus comprises: a pattern projecting means for projecting a cornea shape measuring pattern on the cornea of the eye by using red light or infrared light; a first pickup means for forming an image of the cornea shape measuring pattern formed on the cornea; a curvature calculating means for calculating the respective regional curvatures of regions of the cornea on the basis of the position of the image of the cornea shape measuring pattern determined by processing the image of the cornea shape measuring pattern formed by the first image pickup means; a light projecting means for projecting red light or infrared light into the eye; a second image pickup means for forming an image of the pupil of the illuminated eye by picking up the light projected by the light projecting means and reflected by the interior of the eye; a pupillary information calculating means for calculating information about the pupil on the basis of data obtained by processing the image of the pupil formed by the second image pickup means; and a display means for displaying measured data provided by the curvature calculating means and the pupillary information calculating means.

The display means may be provided with a graphic display means for displaying a corneal curvature distribution pattern and a pattern of the outline of the pupil in a superposed picture.

The ophthalmic apparatus in the second aspect of the present invention may further comprise a fixation target projecting optical system for projecting a pattern of a fixation target on the retina, and a control means for controlling the brightness of the fixation target to keep the pupil size of the eye in a natural state of vision.

The ophthalmic apparatus in the second aspect of the present invention may further comprise an ocular refractive power measuring optical system that projects the pattern of an index on the retina and detects an image of the index reflected by the retina to determine the ocular refractive power of the eye, and the optical paths of the light projecting means may be partly or entirely common with those of the ocular refractive power measuring optical system.

The light source of the light projecting means of the ophthalmic apparatus in the second aspect of the present invention may be used by the ocular refractive power measuring optical system for projecting a measuring index.

The ocular refractive power measuring optical system of the ophthalmic apparatus in the second aspect of the present invention may be provided with a fixation target optical system that fogs the eye, and the fixation target optical system is provided with a control means for controlling the brightness of a fixation target to keep the pupil of the eye in a natural state of vision during pupil measurement.

The ophthalmic apparatus in the second aspect of the present invention may be provided with a transmitting means for transmitting measured data provided by the pupillary information calculating means to a laser keratectomy apparatus.

BRIEF DESCRIPTION OF THE DRAWINGS

The above and other objects, features and advantages of the present invention will become more apparent from the following description taken in connection with the accompanying drawings, in which:

FIGS. 4(a), 4(b), 4(c) and 4(d) are diagrams of assistance in explaining a method of determining the position of the edge of the pupil;

DETAILED DESCRIPTION OF THE PREFERRED EMBODIMENTS

Figure 1:
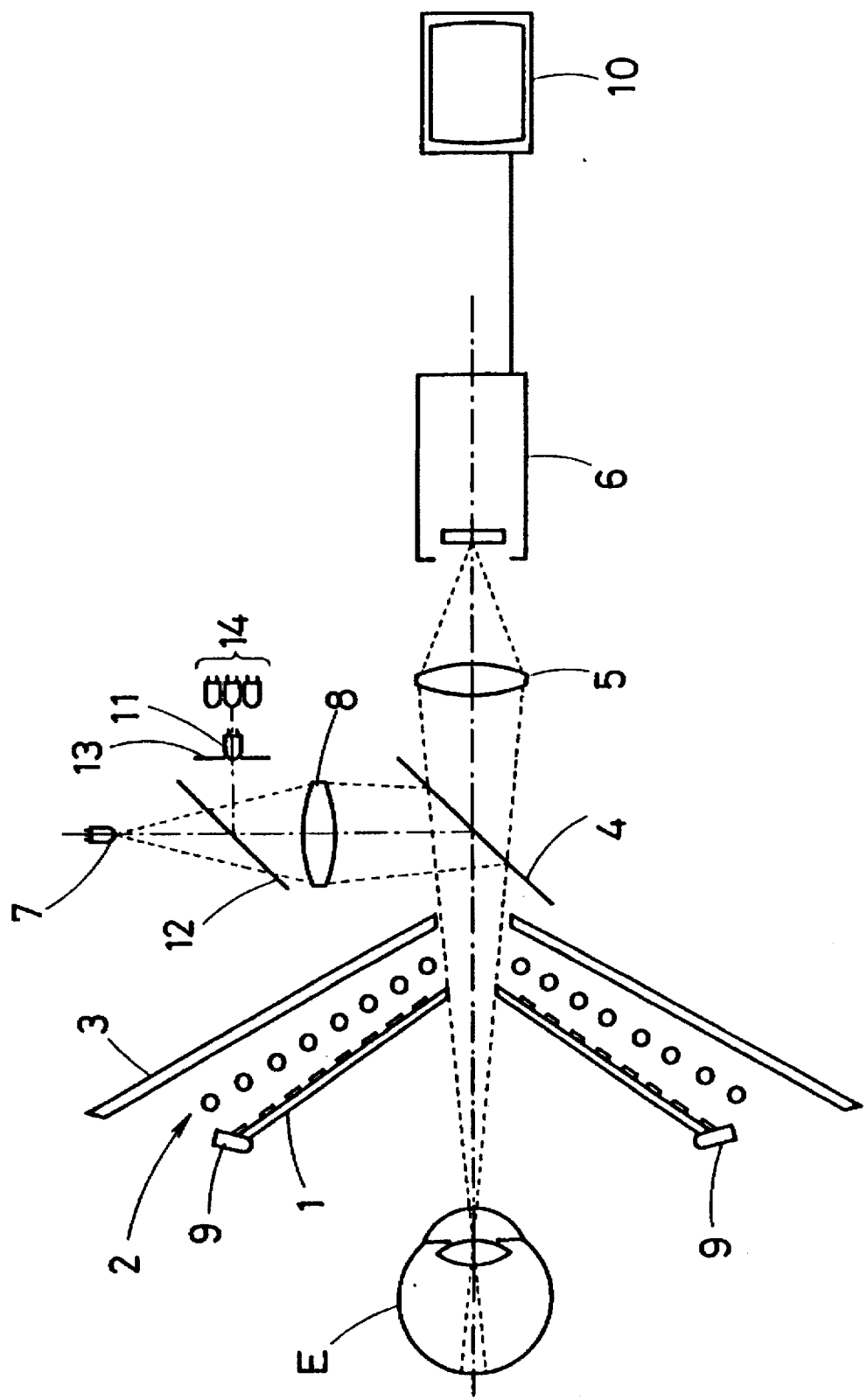
FIG. 1 is a diagrammatic view of optical systems included in an ophthalmic apparatus in a first embodiment according the present invention.

Referring to FIG. 1, an ophthalmic apparatus in a first embodiment according to the present invention has a cornea shape measuring optical system, a pupil measuring optical system and an alignment/observation/display system.

[Cornea Shape Measuring Optical System]

A Placido's disk 1 having a central aperture is provided with a plurality of ring-shaped, concentric, light-transmissive portions of a predetermined width formed coaxially with the optical axis thereof. A plurality of illuminating light sources 2, such as LEDs, that emit light of a wavelength in the wavelength range of red radiation to infrared radiation are arranged behind the light-transmissive portions of the Placido's disk 1. A reflector 3 is disposed behind the illuminating light sources 2 to reflect the light emitted by the illuminating light sources 2 substantially uniformly toward the light-transmissive portions of the Placido's disk 1. The light transmitted through the light-transmissive portions of the Placido's disk is reflected on the surface of the cornea of the eye E and forms an image of the so-called Placido's rings. The light forming the Placido's rings travels through a semitransparent mirror 4 and is focused by an image forming lens 5 in an image of the Placido's rings on the imaging surface of a CCD camera 6. A light-transmissive film that transmits only light of a wavelength in the wavelength range of red radiation to infrared radiation may be disposed in front of the Placido's disk 1 to prevent the contraction of the pupil, and this filter is matted to prevent the reflection of the light from the outside.

[Pupil Measuring Optical System]

An intraocular illuminating light source 7, such as an LED, that emits near-infrared light for illuminating the interior of the eye E is disposed in a substantially conjugate relationship with the iris of the eye E with respect to a condenser lens 8. The light emitted by the intraocular illuminating light source 7 is condensed near the cornea of the eye E to illuminate the interior of the eye E. The light emitted by the intraocular illuminating light source 7 and entered the interior of the eye E is scattered on a fundus of the eye E to illuminate the pupil. The light outgoing through the pupil travels through the semitransparent mirror 4 and is focused on the imaging surface of the CCD camera 6 through the image forming lens.

[Alignment/Observation/Display System]

Anterior part illuminating lamps 9 that emit near-infrared light are built in the Placido's disk 1 to illuminate the anterior part of the eye E for observation. An image of the anterior part of the eye E is formed by the CCD camera 6. A picture corresponding to the image formed by the CCD camera 6 is displayed on a display 10, which is a color liquid crystal display for displaying color pictures, and the picture is used for roughly bringing the optical axis of the ophthalmic apparatus into alignment with the eye E. An alignment light source 11 that emits near-infrared light is disposed so as to be in the focal point of the condenser lens 8. The light emitted by the alignment light source 11 is reflected by the cornea and forms a cornea-reflected bright spot. The position of the ophthalmic apparatus relative to the eye E is adjusted so that the cornea-reflected bright spot is in a predetermined positional relation with a collimating mark, not shown. A fixation target disk 13 has a central aperture to pass alignment light, and a ring slit. The ring slit serves as a fixation target and as a complement to a central light-transmissive portion of the Placido's disk 1 which is expected to be formed in an area corresponding to the central aperture of the Placido's disk 1. An illuminating light source 14 emits light of a wavelength in the wavelength range of red radiation to infrared radiation. The intensity of the light emitted by the illuminating light source 14 is adjusted such that the glare is not caused on the surgery eye when being exposed to the head light on the load in the dark or at twilight, and such that the pupil condition is made in these visual circumstance. The pupil in a state in the dark is measured by turning off the illuminating light source 14.

Figure 2:
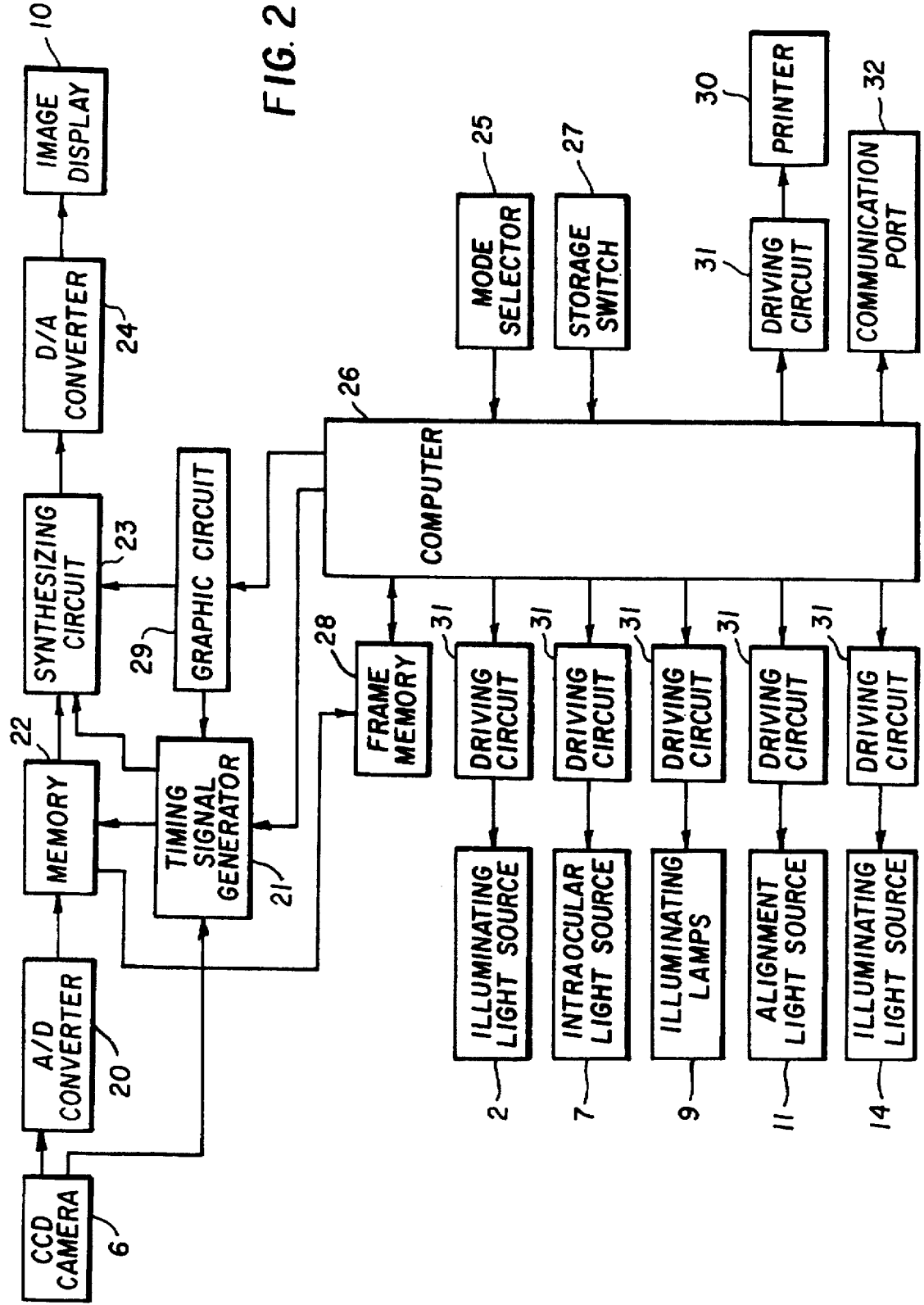
FIG. 2 is a block diagram of a control system included in the ophthalmic apparatus in the first embodiment.

Referring to FIG. 2 showing a control system included in the ophthalmic apparatus of FIG. 1, image signals provided by the CCD camera 6 are converted into corresponding digital image signals by an A/D converter 20, and the digital signals are stored temporarily in a memory 22 in synchronism with a timing signal generated by a timing signal generator 21. The digital image signals stored in the memory 22 are processed by a synthesizing circuit 23 and a D/A converter 24 and an image represented by the processed image signals is displayed on the display 10 in a substantially real-time mode. A mode selector 25 for selecting either a cornea shape measuring mode or a pupil measuring mode is provided with switches for selecting measuring items, and a switch for specifying a continuous operation for measuring the shape of the cornea and the pupil. Signals provided by operating the switches of the mode selector 25 are given to a computer 26. An image storage switch 27 is operated to store the image data and stored in the memory 22, in a frame memory 28. A video graphic circuit 29 generates graphic signals representing video graphics and characters. The display 10 displays a graphic of the shape of the cornea and a synthetic image formed by synthesizing an image formed by the CCD camera 6 and characters showing measured data. The video graphic circuit 29 generates a collimating mark for alignment electrically. Shown also in FIG. 2 are a printer 30, a driving circuit 31 and an RS-232C communication port 32 for transmitting measured data to a keratectomy apparatus or such.

Figure 3A:
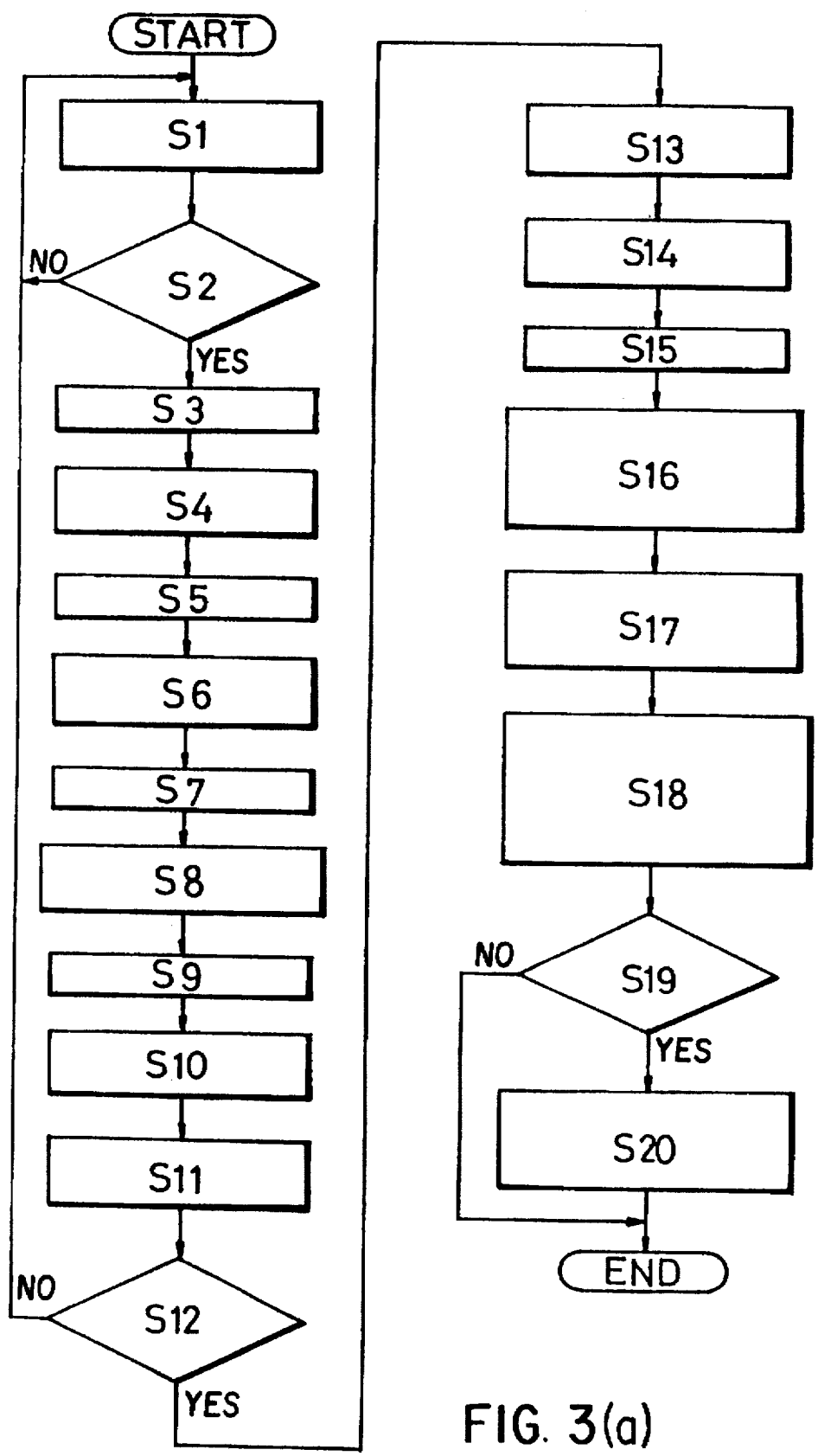
FIG. 3 is a flow chart of assistance in explaining the operation of the ophthalmic apparatus in the first embodiment.

The operation of the ophthalmic apparatus thus constructed in a continuous measuring mode, in which the measurement of the pupil and that of the shape of the cornea are carried out continuously, will be described with reference to a flow chart shown in FIG. 3.

When the continuous measuring mode is selected, the computer 26 turns on the anterior part illuminating lamps 9 and the alignment light source 11. An image of the anterior part of the eye E formed by the CCD camera 6 is stored temporarily in the memory 22, the image is processed by the synthesizing circuit 23 and the D/A converter, and the processed image is displayed on the display 10. The operator adjusts the position of the measuring optical system by operating a known positioning mechanism included in the ophthalmic apparatus referring to the image displayed on the display 10 to position the image of the anterior part of the eye E in a positional relation with the bright spot of the light emitted by the alignment light source 11 and the collimating mark formed by the video graphic circuit 29.

After the measuring optical system has been aligned with the eye E, the image storage switch 27 is operated. Then, the computer 26 turns off the anterior part illuminating lamps 9 and the alignment light source 11, and turns on the intraocular illuminating light source 7 for a predetermined time. The light emitted by the intraocular illuminating light source 7 is condensed near the cornea and illuminates the interior of the eye E. Then, the CCD camera 6 forms an image of the pupil of the internally illuminated eye E. The data of the image of the pupil is stored temporarily in the memory 22, and the computer stores the data of the image of the pupil stored in the memory 22 later in the frame memory 28. After the data of the image of the pupil has been stored, the computer 26 turns on the illuminating light sources 2 for illuminating the Placido's disk 1 for a predetermined time. The illuminating light passed through the Placido's disk 1 falls on the eye E, is reflected by the surface of the cornea and forms reflected images of the Placido's rings. The reflected images are picked up by the CCD camera 6, the image data of the reflected image is stored in the memory 22, and then stored in the frame memory 28.

Since the process for picking up the image of the pupil, storing the image data into the memory, picking up the images of the Placido's rings and storing the image data are accomplished in an moment, the ophthalmic apparatus is able to acquire those image data substantially in the same state of alignment.

The reflected images of the Placido's rings corresponding to the image data stored in the frame memory 28 are displayed on the display 10 to enable the operator to examine the condition of the image. If the images are unsatisfactory, a cancellation switch is operated to repeat those operations for forming the image. If the images are satisfactory, a save switch is operated to save the image data. When the image data is thus saved, the computer 26 starts data processing operations to calculate the diameter of the pupil and the regional curvatures of the cornea.

A method of determining the edge of the pupil will be described with reference to FIGS. 4(a) to 4(d). FIG. 4(a) shows the image of the pupil represented by the image data stored in the frame memory 28, and FIG. 4(b) shows a video signal representing a portion of the eye E on a scanning line L. To determine the edge of the pupil, i.e., the boundary between the pupil (bright area) and the iris (dark area), the waveform of the signal shown in FIG. 4(b) is differentiated. A signal of a waveform shown in FIG. 4(c) obtained by differentiating the waveform of the signal shown in FIG. 4(b) has positive and negative peaks. The waveform of the signal shown in FIG. 4(c) is squared to obtain a signal of a waveform shown in FIG. 4(d) having positive peaks. In FIG. 4(d), suppose that the positions of the edges of 2 peaks are at half the heights e1 and e2, respectively. Then, pixels n1 and n2 correspond to the intersection points of the edge of the pupil and the scanning line L. The number of pixels in the interval between the pixels n1 and n2 is counted. Then, the interval between the pixels n1 and n2, i.e., the diameter d of the pupil, can be calculated by using expression:

$$d = n * K * M$$

where n is the number of pixels in the interval between the pixels n1 and n2, K is the length of one pixel, and M is the optical magnification. Since the values of K and M are known values specific to the ophthalmic apparatus, the diameter d of the pupil can be determined when the number n of pixels in the interval between the pixels n1 and n2 is counted. The center of the pupil is determined to determine the outline of the pupil and the diameters along different diametrical directions.

The positional adjustment of the ophthalmic apparatus relative to the eye E to align the ophthalmic apparatus with the eye E is made with reference to the positional relation between the bright spot of the light emitted by the alignment light source 11, the image of the anterior part of the eye E, and the collimating mark displayed at a predetermined position on the display 10. Therefore, the center of the collimating mark is assumed to be the tentative center of the pupil, i.e., a reference point for determining the edge, and the coordinates of the intersection points of diametrical lines extending across the tentative center at predetermined angular intervals of, for example, 1°, and the edge are determined from the data stored in the memory. The coordinates of the true center of the pupil is determined from a quadratic curve formed by successively connecting the points indicated by the coordinates, and then the coordinates with respect to the tentative center are transformed into those with respect to the true center. Diameters along different angular directions are determined on the basis of the coordinates with respect to the true center, and the coordinates of the center of the pupil and the diameters are stored in the memory of the computer 26. Then, the image data of the images of the Placido's rings are read from the frame memory 28, the edges of the images of the Placido's rings are detected, and the regional curvature of different regions of the cornea are calculated on the basis of the data of the edges of the images of the Placido's rings. When calculating the regional curvatures of different regions of the cornea, the coordinates of the center is calculated on the basis of the coordinates of the edge of the image of the innermost Placido's ring, and the distances between the coordinates of the center and the coordinates of the intersection points of each of diametrical lines extending across the center at predetermined angular intervals of, for example, 1°, and the Placido's rings are calculated. The alignment light source 11 may be turned on during measurement and the bright spot of the light emitted by the alignment light source 11 and reflected by the cornea formed at the center of the innermost Placido's ring may be used as the center of the images of the Placido's rings. In this case, it makes possible to calculate the shape of the center portion of the cornea exactly and display. After the distances between the coordinates of the center and the intersection points of each diametrical line and the Placido's rings have been calculated, the data of the distances is compared with the data of a sphere having a known curvature to determine the regional curvatures of different regions of the cornea. Refer to U.S. Ser. No. 08/280,192 (Title of the Invention: Ophthalic Apparatus for Measuring Refractive Characteristic of Eye to Be Measured) applied by the applicant of the present patent application for the further details of the method of calculating the curvature of the cornea using the images of the Placido's rings. Since the measurement of the pupil and the measurement of the shape of the cornea are carried out in the same state of alignment of the ophthalmic apparatus with the eye E, the positional relation between the center of the pupil and that of the images of the Placido's rings can be known from the respective coordinates of the center of the pupil and that of the Placido's rings. The measured data of regional curvatures of different regions of the cornea, the measured data of the diameter of the pupil, the center of the pupil, the center of the images of the Placido's rings, the positional relation between the center of the pupil and the images of the Placido's rings thus determined are displayed on the display 10.

Figure 5:
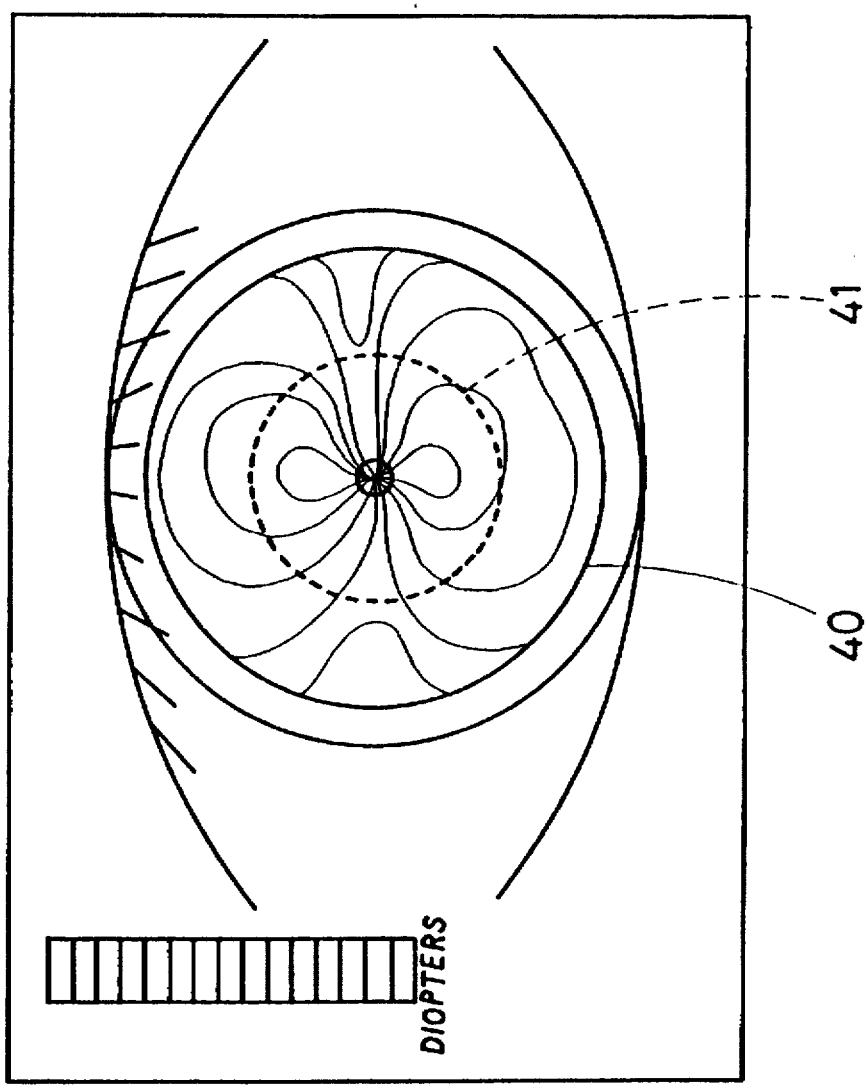
FIG. 5 is a pictorial view of a superposed picture formed on the basis of measured data representing the regional curvatures of the cornea, and the diameter and the center of the pupil, and displayed on a display.

Particulars about the cornea and the pupil to be displayed can be selectively determined by operating a display switch. FIG. 5 shows examples of displayed particulars. In FIG. 5, the distribution of the regional refractive powers of the cornea is displayed in a color map. The regional refractive powers can be obtained by converting the measured regional radii of curvature by a known method of calculation. A dotted circle 41 is the outline of the pupil. The corneal curvature distribution (corneal refractive power distribution) and the outline of the pupil in a natural state of vision are displayed in a superposed picture. Effective information for keratotomic operation can be acquired through the comparative observation of the corneal curvature distribution and the pupil. The data can be displayed in numerical values. The data of the diameter and position of the pupil abovementioned can be sent through the RS-232C communication port 32 to the keratotomic apparatus. When conducting a keratotomic operation utilizing the measured data obtained by this ophthalmic apparatus, the measured data can be surely and correctly transferred through the RS-232C communication port 32 and the measured data enables the efficient operation of the keratotomic apparatus.

Figure 6:
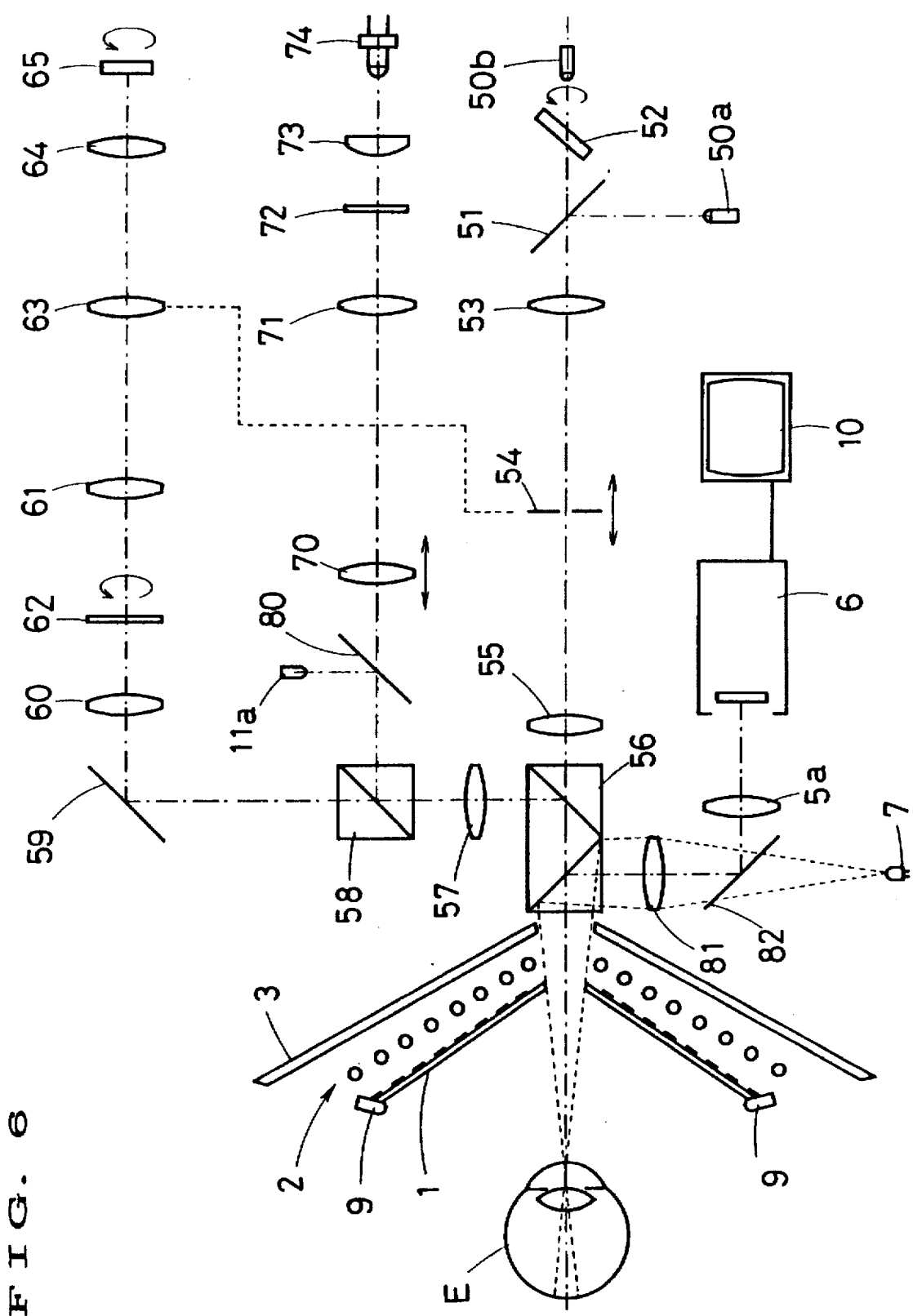
FIG. 6 is a diagrammatic view of optical systems included in an ophthalmic apparatus in a second embodiment according to the present invention.

FIG. 6 shows optical systems included in an ophthalmic apparatus in a second embodiment according to the present invention, in which parts like or corresponding to those of the ophthalmic apparatus in the first embodiment are designated by the same reference characters. The ophthalmic apparatus in the second embodiment comprises, in addition to the components of the ophthalmic apparatus in the first embodiment, an ocular refractive power measuring system.

Referring to FIG. 6, measuring light sources 50a and 50b that emit near-infrared light are disposed on optical axes with respect to a semitransparent mirror 51. A parallel-plane glass 52 is disposed at an angle to a plane perpendicular to the optical axis so as to turn about the optical axis. The light emitted by the measuring light source 50b is biased from the optical axis and turned by the parallel-plane glass 52. The measuring light sources 50a and 50b are disposed near positions corresponding to the front focal point of a condenser lens 53. Shown also in FIG. 6 are spot diaphragm 54 capable being moved to a position in a conjugate relationship with the retina of the eye E, a projection lens 55, a beam splitter 56, an objective lens 57, a beam splitter 58, a mirror 59, relay lenses 80 and 81, a band-shaped corneal reflection eliminating mask 82 disposed at a position in a conjugate relationship with the cornea of the eye E, a movable lens 63 capable of moving together with the spot diaphragm 54, an image forming lens 64, a measuring light receiving device 65 that rotates in synchronism with the parallel-plane glass 52 and the corneal reflection eliminating mask 62, a first relay lens 70 that moves along the optical axis to fog the eye E, a second relay lens 71, a fixation target 72 disposed at the focal point of the second relay lens 71, a condenser lens 73, an illuminating lamp 74, a semitransparent mirror 80, an alignment light source 11a that emits near-infrared light, disposed at a position behind the beam splitter 58 and the semitransparent mirror 80 and corresponding to the focal point of the objective lens 57, an objective lens 81, a semitransparent mirror 82, and an image forming lens 5a. An intraocular illuminating light source 7 illuminates the eye E through the semitransparent mirror 82 and the beam splitter 56 to obtain an image of the pupil. The respective images of the pupil and the Placido's rings are formed through the beam splitter 56, the semitransparent mirror 82, the objective lens 81 and the image forming lens 5a on the imaging surface of a CCD camera 6.

When determining the ocular refractive power by the ophthalmic apparatus having the aforesaid optical systems, measuring light emitted by the measuring light sources 50a and 50b is condensed near the cornea of the eye E by the condensing lens 53, the spot diaphragm 54 and the projection lens 55 and falls on the retina. The light reflected by the retina is deflected by the beam splitter 56, is reflected by the mirror 59, travels through the relay lenses 60 and 61 and is focused on the image forming surface of the light receiving device 65 by the image forming lens 64. The spot diaphragm 54 is moved together with the movable lens 63 according to the output signal of the light receiving device 65 to position the spot diaphragm 54 at a position in a conjugate relationship with the retina of the eye E. The position of the first relay lens 70 is adjusted so that the fixation target 72 is positioned at a position in a conjugate relationship with the retina of the eye E, and then the first relay lens 70 is moved by a distance corresponding to an appropriate diopter for fogging. After thus fogging the eye E, the parallel-plane glass 52 is turned through an angle of 360° at a predetermined angular step of, for example, 1°. The spot diaphragm 54 and the movable lens 63 are moved according to signals provided by the light receiving device 65 while the parallel-plane glass 52 is being turned to determine refractive powers with respect to all directions from the distance of movement of the spot diaphragm 54. The refractive powers thus determined are displayed graphically on the display 10. The refractive powers, similarly to the corneal curvature distribution, may be displayed in a color map. Refer to U.S. Ser. No. 08/280,192 (Title of the Invention: Ophthalic Apparatus for Measuring Refractive Characteristic of Eye to Be Measured) applied by the applicant of the present patent application for the further details of the method of displaying the refractive powers.

Figure 7:
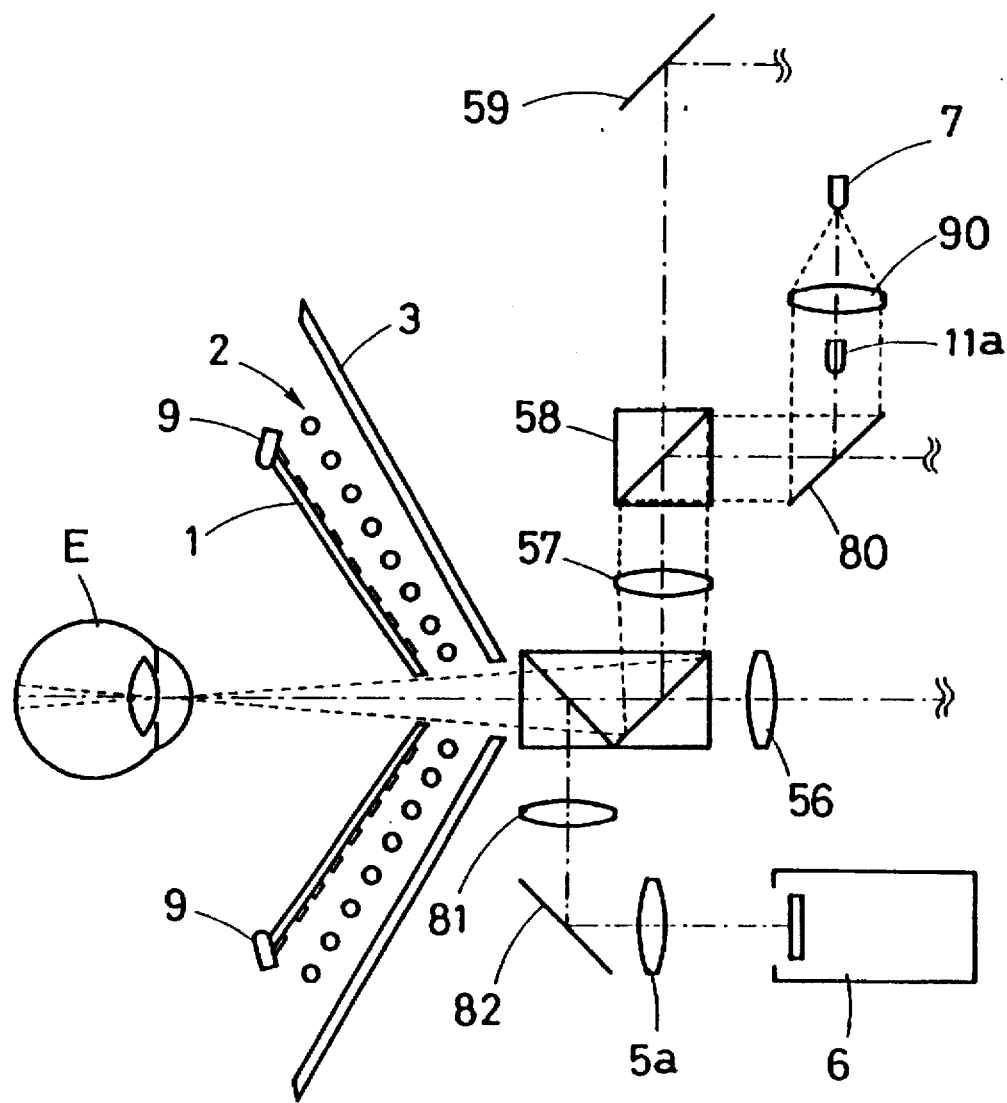
FIG. 7 is a diagrammatic view of a modification of the ophthalmic apparatus in the second embodiment.

In a modification of the ophthalmic apparatus in the second embodiment, an intraocular illuminating light source 7 is disposed on the side of the fixation target projector as shown in FIG. 7. The intraocular illuminating light source 7 is disposed behind a condenser lens 90 disposed behind an alignment light source 11a so that the intraocular illuminating light source 7 is in a conjugate relationship with the iris of the eye E.

In another modification of the ophthalmic apparatus in the second embodiment, the measuring light source 50a is used also as an intraocular illuminating light source. Only the measuring light source 50a is turned on and the spot diaphragm 54 is positioned at a position nearest to the measuring light source 50a when forming an image of the pupil, so that the light emitted by the measuring light source 50a can be efficiently guided into the eye E and, consequently, a bright image of the pupil can be formed.

The measurement of the pupil in a natural state of vision and in the dark can be measured by controlling the intensity of the light emitted by the illuminating lamp 74 for illuminating the fogging fixation target. In this case, any additional light source for illuminating the fixation target is not necessary.

Although the invention has been described in its preferred forms with a certain degree of particularity, obviously many changes and variations are possible therein. It is therefore to be understood that the present invention may be practiced otherwise than as specifically described herein without departing from the scope and spirit thereof.

What is claimed is:

1. An ophthalmic apparatus comprising:
   an index pattern projecting means for projecting the pattern of a cornea shape measuring index for measuring the shape of the cornea on the cornea;
   a first image pickup means for forming an image of the index for measuring the shape of the cornea;
   a cornea shape calculating means for calculating the respective shapes of regions of the cornea on the basis of the position of the image of the index determined by processing the image formed by said first image pickup means;
   a pupil illuminating means for illuminating the pupil of the eye with red light or infrared light;
   a second image pickup means for forming an image of the pupil illuminated by said pupil illuminating means;
   a fixation target projecting means for indicating a fixation target on the eye to be examined, said fixation target projecting means including an adjustment means for adjusting the brightness of the fixation target so as to adjust the level of the contraction of the pupil of the eye to be examined when the pupil is measured;
   a pupil measuring means for measuring the shape or the size of the pupil on the basis of the position of the edge of the pupil determined by processing the image formed by said second image pickup means; and
   a control means for controlling the operation of said cornea shape calculating means and said pupil measuring means to measure the pupil and the cornea shape successively in a measuring mode.

2. An ophthalmic apparatus according to claim 1, wherein said first image pickup means is used also as said second image pickup means.

3. An ophthalmic apparatus comprising:
   a pattern projecting means for projecting a cornea shape measuring pattern on the cornea of the eye by using red light or infrared light;
   a first image pickup means for forming an image of the cornea shape measuring pattern formed on the cornea;
   a curvature calculating means for calculating the respective regional curvatures of regions of the cornea on the basis of the position of the image of the cornea shape measuring pattern determined by processing the image of the cornea shape measuring pattern formed by said first image pickup means;
   a light projecting means for projecting red light or infrared light into the eye through a pupil of the eye;
   a second image pickup means for forming an image of the pupil of the illuminated eye by picking up the light projected by said light projecting means and reflected by a fundus of the eye;
   a fixation target projecting means for indicating a fixation target on the eye to be examined, said fixation target projecting means including means for emitting a certain quantity of light for restricting the contraction of the pupil of the eye to be examined when the pupil is measured;
   a pupillary information calculating means for calculating information about the pupil on the basis of data obtained by processing the image of the pupil formed by said second image pickup means; and
   a display means for displaying measured data provided by said curvature calculating means and said pupillary information calculating means.

4. An ophthalmic apparatus according to claim 3, wherein said display means may be provided with a graphic display means for displaying a corneal curvature distribution pattern and a pattern of outline of the pupil in a superposed picture.

5. An ophthalmic apparatus according to claim 3 further comprising: a fixation target projecting optical system for projecting a pattern of a fixation target on the retina, said fixation target projecting means including an adjustment means for adjusting the brightness of the fixation so as to adjust the level of the contraction of the pupil of the eye to be examined, and a control means for controlling the brightness of the fixation target to keep the pupil size of the eye in a natural state of vision.

6. An ophthalmic apparatus according to claim 3 further comprising an ocular refractive power measuring optical system that projects the pattern of an index on the retina and detects an image of the index reflected by the retina to determine the ocular refractive power of the eye, the optical paths of said light projecting means being partly or entirely common with those of said ocular refractive power measuring optical system.

7. An ophthalmic apparatus according to claim 6, wherein the light source of said light projecting means is used by said ocular refractive power measuring optical system for projecting the measuring index.

8. An ophthalmic apparatus according to claim 6, wherein said ocular refractive power measuring optical system is provided with a fixation target optical system that fogs the eye, and said fixation target optical system is provided with a control means for controlling the brightness of the fixation target to keep the pupil size of the eye in a natural state of vision during pupil measurement.

9. An ophthalmic apparatus according to claim 3 further comprising a transmitting means for transmitting measured data provided by said pupillary information calculating means to a laser keratectomy apparatus.

10. An ophthalmic apparatus comprising:
    a cornea shape measuring optical system for illuminating a Placido's disk with red or infrared light into the eye through a pupil of the eye and detecting a reflected image reflected by a fundus of the eye;
    a pupil measuring optical system for illuminating the interior of the eye with red or infrared light to illuminate a pupillary region and obtaining an image of the pupillary region;
    a mode selecting means for selecting either a cornea shape measuring mode or a pupil measuring mode; and
    a cornea/pupil data calculating means for calculating cornea curvature data on the basis of data obtained by processing the reflected image of the Placido's disk obtained by illuminating the cornea with red or infrared light by said cornea shape measuring optical system in the cornea shape measuring mode and calculating pupil data on the basis of data obtained by processing the image of the pupillary region obtained by illuminating the interior of the eye with red or infrared light in the pupil measuring mode.

11. An ophthalmic apparatus according to claim 10, wherein said cornea shape measuring optical system and said pupil measuring optical system share a common detecting means.

12. An ophthalmic apparatus according to claim 10 further comprising a display means for displaying measured data provided by said cornea/pupil data calculating means.

13. An ophthalmic apparatus according to claim 12, wherein said display means has a graphic displaying means capable of displaying a corneal curvature distribution pattern and the pattern of the outline of the pupil in a superposed picture.

14. An ophthalmic apparatus according to claim 10 further comprising an alignment/observation optical system which illuminates the anterior part of the eye for observation.

15. An ophthalmic apparatus according to claim 10 further comprising a continuous measurement mode selecting means for selecting a continuous measurement mode in which operations in the pupil measuring mode and the cornea shape measuring mode are carried out continuously.

* * * * *